(12) United States Patent
Yamaguchi (10) Patent No.: US 9,741,548 B2
(45) Date of Patent: Aug. 22, 2017

(54) MASS SPECTROMETER (71) Applicant: SHIMADZU CORPORATION, Kyoto-shi, Kyoto (JP)

(72) Inventor: Shinichi Yamaguchi, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 0 days.

(21) Appl. No.: 15/117,868

(22) PCT Filed: Jul. 3, 2014

(86) PCT No.: PCT/JP2014/067791
§ 371 (c)(1),
(2) Date: Aug. 10, 2016

(87) PCT Pub. No.: WO2016/002045
PCT Pub. Date: Jan. 7, 2016

(65) Prior Publication Data
US 2017/0011897 A1 Jan. 12, 2017

(51) Int. Cl.
H01J 49/00 (2006.01)
G01N 30/72 (2006.01)
(Continued)

(52) U.S. Cl.
CPC ........ *H01J 49/0009* (2013.01); *G01N 30/724* (2013.01); *H01J 49/0422* (2013.01);
(Continued)

(58) Field of Classification Search
CPC .. H01J 49/0009; H01J 49/0422; H01J 49/165; H01J 49/0445; G01N 30/724; G01N 2030/626
(Continued)

(56) References Cited

U.S. PATENT DOCUMENTS

| 2002/0121598 A1* | 9/2002 | Park | H01J 49/165 250/288 |
| 2009/0008548 A1* | 1/2009 | Yamaguchi | G01N 30/72 250/288 |
| 2015/0008310 A1* | 1/2015 | Ledford, Jr. | H01J 49/0009 250/252.1 |

FOREIGN PATENT DOCUMENTS

| JP | 10-132786 A | 5/1998 |
| JP | 2000-057989 A | 2/2000 |
| JP | 2013-521470 A | 6/2013 |

OTHER PUBLICATIONS

International Search Report of PCT/JP2014/067791 dated Sep. 2, 2014.

* cited by examiner

*Primary Examiner* — Michael Maskell
(74) *Attorney, Agent, or Firm* — Sughrue Mion, PLLC (57) ABSTRACT

The mass spectrometer (1) provides an ionization chamber (11) therein with: a probe (15) having a sample to be measured flow path (155) for spraying a sample to be measured; and a standard sample flow path (255) for spraying a standard sample used for the calibration of the mass-to-charge ratio of the mass spectrum into the ionization chamber. The standard sample is intermittently introduced into the ionization chamber via a pulse valve (216). Thus, mixing of the sample to be measured and the standard sample can be prevented, while the timing according to which the standard sample is introduced can be appropriately controlled. It also becomes possible to acquire an accurate mass spectrum for each sample to be measured even in the case where a number of types of samples to be measured are introduced into the ionization chamber one after another over a short period of time.

3 Claims, 6 Drawing Sheets (51) Int. Cl.
*H01J 49/04* (2006.01)
*H01J 49/16* (2006.01)
*G01N 30/62* (2006.01)

(52) U.S. Cl.
CPC ........ *H01J 49/0445* (2013.01); *H01J 49/165* (2013.01); *G01N 2030/626* (2013.01)

(58) Field of Classification Search
USPC .................................... 250/281, 282, 288
See application file for complete search history.

Prior Art

MASS SPECTROMETER

TECHNICAL FIELD

The present invention relates to a chromatograph mass spectrometer with which qualitative analysis and quantitative analysis are carried out through chromatography by using a mass spectrometer such as a gas chromatograph mass spectrometer or a liquid chromatograph mass spectrometer as a detector, and in particular, to a calibration method for a mass spectrometry unit in a chromatograph mass spectrometer.

BACKGROUND ART

A liquid chromatograph mass spectrometer (LC/MS) is formed of a liquid chromatograph unit (LC unit) for separating a liquid sample into its respective ingredients that are then eluted, an ionization chamber (interface unit) for ionizing sample ingredients that have eluted from the LC unit, and a mass spectrometry unit (MS unit) for detecting the ions that have been introduced from the ionization chamber. In such an ionization chamber, various ionization techniques are used in order to ionize sample ingredients, and atmospheric pressure ionization methods such as atmospheric pressure chemical ionization (APCI) and electrospray ionization (ESI) are widely used.

In typical APCI, the end of a nozzle that is connected to the terminal of a column in the LC unit is arranged so as to be directed toward the inside of the ionization chamber, and at the same time, a needle electrode is placed in front of the end of the nozzle. Thus, a droplet of the sample that has been atomized through the application of heat in the nozzle is chemically responded to carrier gas ions (buffer ions) that have been generated through corona discharge from the needle electrode and is ionized. In ESI, the end of a nozzle that is connected to the terminal of a column in the LC unit is arranged so as to be directed toward the inside of the ionization chamber, and at the same time, a high voltage of approximately several kV is applied to the end of the nozzle so as to generate a strong non-uniform electric field. As a result, the sample ingredients are charge separated by the electric field and torn off due to Coulomb attraction, and thus are atomized. Consequently, the solvent in the droplet of the sample is evaporated upon contact with the ambient air, and thus, gas ions are generated.

In the above-described APCI and ESI, the sample ingredients are ionized in a state that is close to the atmospheric pressure, and therefore, a difference in the pressure is secured between the ionization chamber in a high pressure state (that is to say, a state that is close to the atmospheric pressure) and the MS unit in a state of very low pressure (that is to say, a state that is highly vacuumed), and thus, such a configuration is adopted that middle chambers are provided between the ionization chamber and the MS unit so that the degree of vacuuming is increased step by step.

Figure 4:
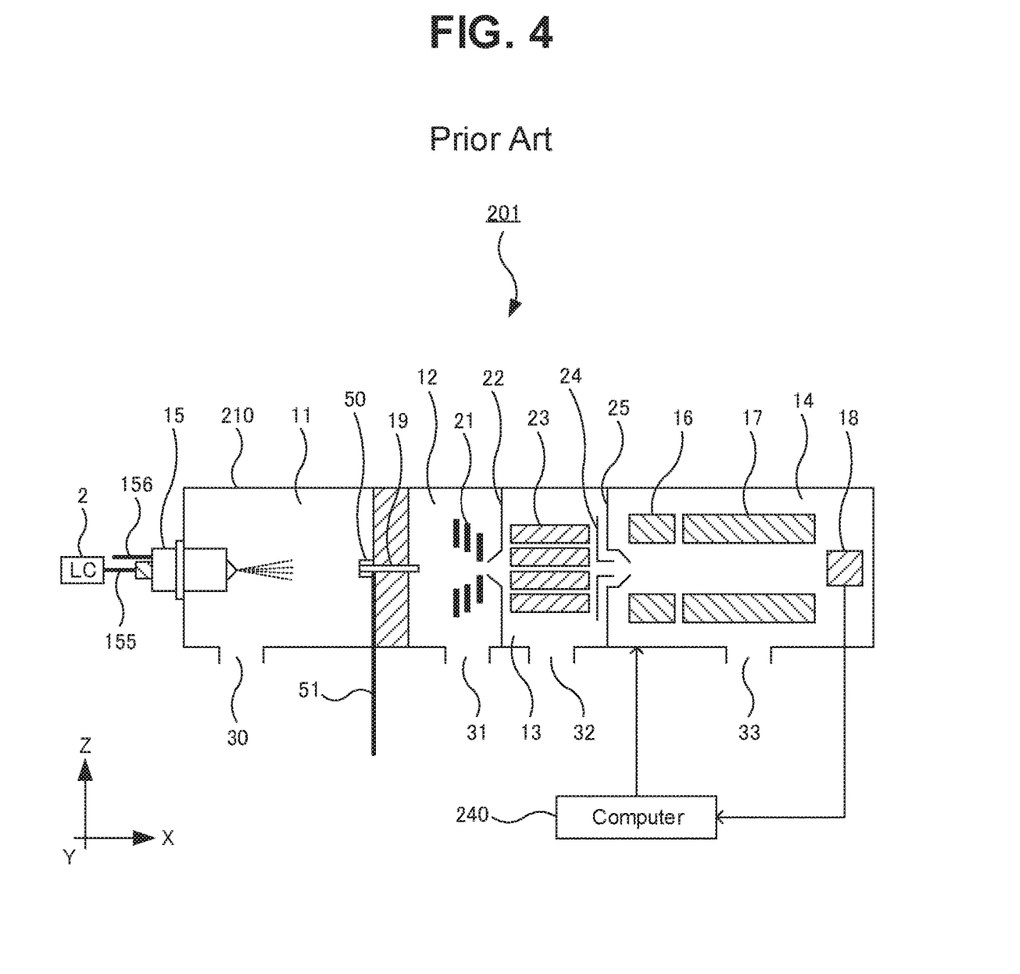
FIG. 4 is a schematic diagram showing the structure of an example of a liquid chromatograph mass spectrometer using an ESI method.

FIG. 4 is a schematic diagram illustrating the structure of an example of a liquid chromatograph mass spectrometer using an ESI method. Here, the forward direction that is parallel to the ground is the X direction, the direction that is parallel to the ground and perpendicular to the X direction is the Y direction, and the direction that is perpendicular to the X direction and the Y direction is the Z direction.

A liquid chromatograph mass spectrometer 201 is provided with an LC unit 2, a probe (ion source) 15, an ionization chamber 11 having a chamber (housing) 210, a first middle chamber 12 that is adjacent to the ionization chamber 11, a second middle chamber 13 that is adjacent to the first middle chamber 12, a mass spectrometry chamber (MS unit) 14 that is adjacent to the second middle chamber 13, and a computer 240 that controls the entirety of the liquid chromatograph mass spectrometer 201.

Each sample to be measured (sample ingredient) that is gained by separating a sample into ingredients in the LC unit 2 is supplied through a sample to be measured flow path 155, and a nebulizing gas (nitrogen gas) is supplied through a nebulizing gas flow path 156. As a result, the liquid sample and the nebulizing gas are led to a probe 15 so as to be sprayed.

Figure 5A:
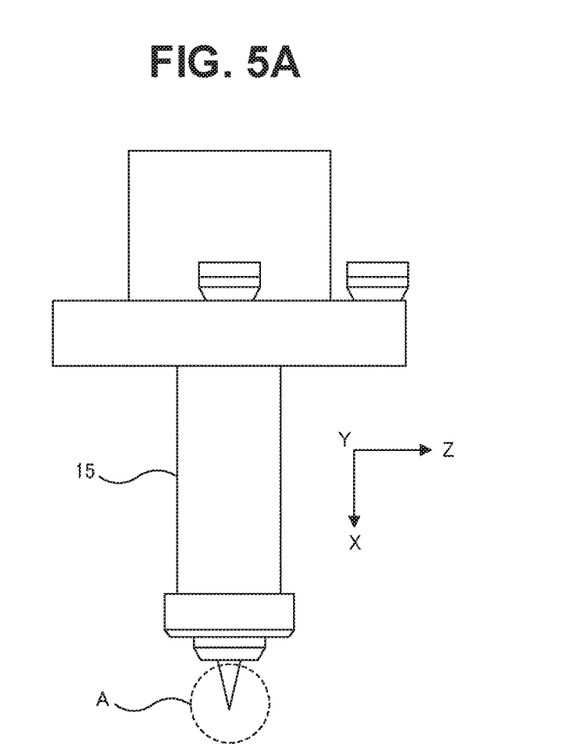
FIG. 5A is a side diagram showing a probe.
Figure 5B:
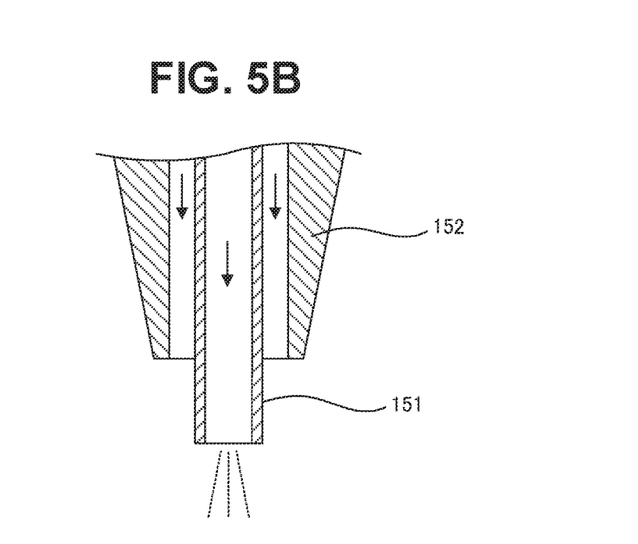
FIG. 5B is a cross-sectional diagram showing an enlargement of A in FIG. 5A.

FIG. 5A is a side diagram showing a probe, and FIG. 5B is a cross-sectional diagram showing an enlargement of A in FIG. 5A. The probe 15 has a double tube structure where a sample to be measured that has been supplied through the sample to be measure flow path 155 is sprayed from the inside of a circular tube 151. Meanwhile, a nitrogen gas that has been supplied through the nebulizing gas flow path 156 is sprayed between the circular tube 151 and a nozzle 152 in a circular tube form. As a result, the sprayed sample to be measured is sprayed in an atomized state resulting from the collision effects with the nebulizing gas that is sprayed from the side around the circular tube 151.

Though not shown, wires are connected so that a high voltage of several kV can be applied to the end of the nozzle 152 from the voltage supply, and such a configuration makes ionization possible. The housing of the ionization chamber 11 is a chamber 210 in a rectangular parallelepiped form of 13 cm×13 cm×12 cm, which has an upper wall, a partition (rear wall), a front wall, a right side wall, a left side wall and a lower wall. Thus, the space inside the ionization chamber 11 is surrounded by the upper wall, the partition (rear wall), the front wall, the right side wall, the left side wall and the lower wall.

A circular opening that runs in the forward and backward direction (X direction) is created in the front wall so that a probe 15 can be attached in the opening.

The partition is provided between the ionization chamber 11 and the first middle chamber 12, and a solvent releasing tube (ion introducing tube) 19 in circular tube form (having an outer diameter of 1.6 mm and an inner diameter of 0.5 mm) is formed in the partition, and a dry gas flow path 50 is formed so as to cover the periphery of the solvent releasing tube 19. As a result, the inside of the ionization chamber 11 and the inside of the first middle chamber 12 communicate through the solvent releasing tube 19. In addition, the solvent releasing tube 19 functions to promote the release of the solvent and ionization through the application of heat and the collision effects when the ions and a droplet of a microscopic sample that have been sprayed by the probe 15 pass through the inside of the solvent releasing tube 19.

The nozzle of the probe 15 is directed toward the front (X direction) so as to face the entrance of the solvent releasing tube 19 with a predetermined distance (2 cm, for example) in between.

A drain 30 is created in the lower wall so that unnecessary samples can be discharged to the outside through the drain 30.

A first ion lens 21 is provided inside the first middle chamber 12, and an exhaust outlet 31 for vacuum exhaust using an oil-sealed rotary pump (RP) is provided in the lower wall of the first middle chamber 12. In addition, a skinner 22 having an orifice is formed in the partition between the first middle chamber 12 and the second middle chamber 13 so that the inside of the first middle chamber 12 and the inside of the second middle chamber 13 communicate through this orifice.

An octupole 23 and a focus lens 24 are provided inside the second middle chamber 13, and an exhaust outlet 32 for vacuum exhaust using a turbo molecular pump (TMP) is provided in the lower wall of the second middle chamber 13. In addition, an entrance lens 25 having an orifice is provided in the partition between the second middle chamber 13 and the mass spectrometry chamber 14 so that the inside of the second middle chamber 13 and the inside of the mass spectrometry chamber 14 communicate through this orifice.

A first quadrupole 16, a second quadrupole 17 and a detector 18 are provided inside the mass spectrometry chamber 14, and an exhaust outlet 33 for vacuum exhaust using a turbo molecular pump (TMP) is provided in the lower wall of the mass spectrometry chamber 14.

Here, the ion lens 21, the octupole 23, the focus lens 24 and the entrance lens 25 have convergence effects with which the ions that pass at respective ion velocities under the respective vacuum states are efficiently sent to the next stage.

In such a liquid chromatograph mass spectrometer, the ions generated in the ionization chamber 11 sequentially pass through the solvent releasing tube 19, the first ion lens 21 within the first middle chamber 12, the skinner 22, the octupole 23 and the focus lens 24 within the second middle chamber 13, and the entrance lens 25 so as to be sent to the mass spectrometry chamber 14, where the ions are separated depending on the size of the mass-to-charge ratio (m/z) by the quadrupoles 16 and 17 and reach the detector 18.

The computer 240 acquires intensity signals that correspond to the number of generated ions for each mass-to-charge ratio (m/z) so as to create a mass spectrum. As a result, the molecular weight of the sample to be measured is calculated from the mass-to-charge ratio (m/z) where a peak of the molecular ions appears in the mass spectrum. In addition, as for the fragment ions that are generated when the molecular ions are split, the manner of splitting is estimated from the mass-to-charge ratio (m/z) where a peak of each fragment ion type appears, and the molecular structure of the sample to be measured is analyzed.

Incidentally, in the above-described liquid chromatograph mass spectrometer 201, the value gained by measuring the mass spectrum changes as time elapses, and therefore, the mass-to-charge ratio (m/z) for each peak that is gained by measuring a sample is determined by using a peak that is gained by measuring a standard sample (calibration sample) of which the value is already known for a predetermined period of time (see Patent Literature 1). Typically, the difference (calibration value) between the value of the mass-to-charge ratio (m/z) for each peak that is gained by measuring a standard sample and the theoretical value of the mass-to-charge ratio (m/z) for the corresponding peak is calculated for each peak so that a calibration value can be found for any mass-to-charge ratio (m/z) by interpolating or extrapolating these calibration values. Thus, the calibration value is added to the value of the mass-to-charge ratio (m/z) for a peak that is gained by measuring a sample to be measured so that a precise mass-to-charge ratio (m/z) can be calculated for each peak.

In the case where mass spectrometry is carried out by mixing a sample to be measured and a standard sample (internal standard method), however, the efficiency in the ionization in the electrospray ion source (probe 15) is different between the respective samples, and in addition, only one sample is often ionized when mixed.

Therefore, a method for carrying out mass spectrometry on a sample to be measured and a standard sample "almost at the same time" or "separately" has been disclosed. Examples are a method for introducing a standard sample into the sample to be measured flow path 155 separately timewise (see Patent Literature 2), a method for mechanically switching the directions in which ions are introduced using a device for a number of types of ions (see Patent Literature 3), and a method for introducing a standard sample into a vacuum through a flow path that is different from the sample to be measured flow path 155.

CITATION LIST

Patent Literature

Patent Literature 1: Japanese Unexamined Patent Publication H10 (1998)-132786
Patent Literature 2: Japanese Translation of PCT International Patent Publication 2013-521470
Patent Literature 3: Japanese Unexamined Patent Publication 2000-57989

SUMMARY OF INVENTION

Technical Problem

In the above-described methods, however, a mixture is generated or ionization is destabilized when a standard sample is directly introduced into the sample to be measured flow path 155. When a sample to be measured and a standard sample are introduced into different flow paths, a number of types of samples to be measured that have been separated in the LC unit are sequentially introduced into the ionization chamber 11 one after another, and therefore, it is very difficult to control the timing according to which the standard sample is introduced.

Solution to Problem

In order to solve the above-described problems, the present inventor examined an introduction method for introducing a standard sample. Thus, it was determined that a standard sample flow path for spraying a standard sample into the inside of the ionization chamber was to be formed, and a pulse valve was to be arranged in the standard sample flow path so that a standard sample could be introduced intermittently using the pulse valve.

That is to say, the mass spectrometer according to the present invention is provided with an ionization chamber where a sample is ionized, and a mass spectrometry unit into which ions are introduced from the ionization chamber, wherein the above-described ionization chamber has a housing that provides a space inside the housing, a probe having a sample to be measured flow path in order to spray a sample to be measured into the inside of the above-described ionization chamber is attached to the above-described housing, and an ion introducing tube is created in the above-described housing so that the inside of the above-described ionization chamber and the inside of the mass spectrometry unit communicate, a mass spectrum value that is gained by measuring a sample to be measured is calibrated using a mass spectrum value that is gained by measuring a standard sample, and the mass spectrometer is further provided with a standard sample flow path that sprays a standard sample into the inside of the above-described ionization chamber, and a pulse valve that is arranged in the standard sample flow path so as to introduce a standard sample intermittently.

Figure 6:
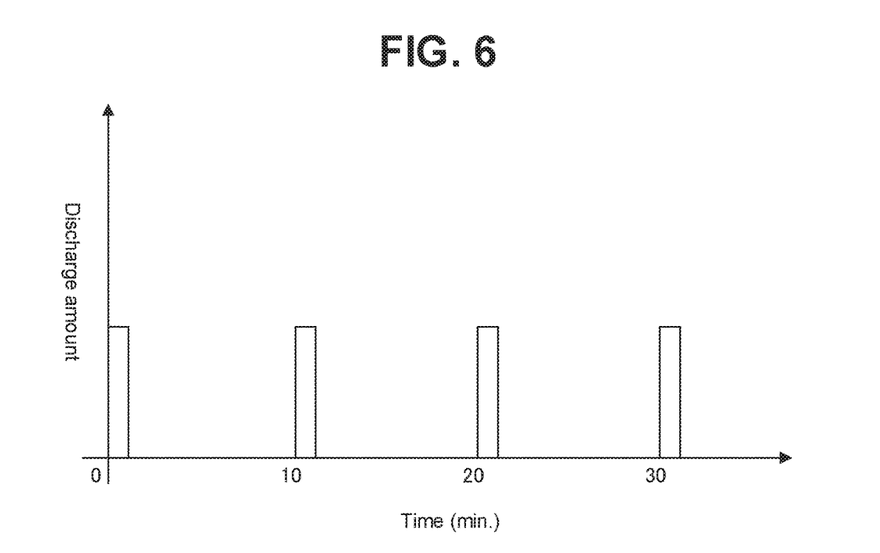
FIG. 6 is a graph showing the relationship between the time and the amount of standard sample that has been discharged into the inside of the ionization chamber.

Here, "intermittently" means that something happens and stops at a certain period of time in between. Therefore, in the mass spectrometer according to the present invention, a standard sample is introduced into the standard sample flow path during the first time slot (0 minutes to 1 minute, for example), and the standard sample is not introduced into the standard sample flow path during the following second time slot (1 minute to 10 minutes, for example), and then, the standard sample is introduced into the standard sample flow path during the following third time slot (10 minutes to 11 minutes, for example). FIG. 6 is a graph showing an example of the relationship between the time and the amount of standard sample that has been discharged into the inside of the ionization chamber. Thus, a standard sample is introduced into the ion introducing tube during the first time slot, a sample to be measured is introduced during the following second time slot, and the standard sample is again introduced during the following third time slot.

As described above, in the mass spectrometer according to the present invention, the timing according to which a standard sample is introduced can be appropriately controlled while preventing a sample to be measured and the standard sample from being mixed. In addition, it is possible to acquire a precise mass spectrum for each sample to be measured even in the case where a number of types of samples to be measured are introduced into the ionization chamber one after another over a short period of time.

In the above-described invention, the above-described standard sample flow path may be arranged so that a standard sample can be sprayed between the spraying nozzle of the above-described sample to be measured flow path and the above-described ion introducing tube.

In the mass spectrometer according to the present invention, the standard sample that has been sprayed into the inside of the ionization chamber blows away a sample to be measured that is moving toward the ion introducing tube so that only the standard sample can be introduced into the ion introducing tube. In addition, the pulse valve can be controlled so as to change the amount of the introduced standard sample when the standard sample is introduced into the standard sample flow path, and as a result, the concentration of the standard sample that is introduced into the ion introducing tube can also be made adjustable. Therefore, the time and effort for adjusting the concentration of the standard sample are unnecessary.

Furthermore, in the above-described invention, the above-described standard sample flow path may be the same flow path as a dry gas flow path that sprays a dry gas or may be the same flow path as a nebulizing gas flow path that sprays a nebulizing gas.

In the mass spectrometer according to the present invention, it is not necessary to form a new standard sample flow path. In addition, the amount of introduced standard sample can be changed by controlling the pulse valve when the standard sample is introduced into the standard sample flow path, and as a result, the concentration of the standard sample that is introduced into the ion introducing tube can also be made adjustable. Therefore, the time and effort for adjusting the concentration of the standard sample are unnecessary.

Moreover, in the above-described invention, the above-described standard sample flow path may be the same flow path as the above-described sample to be measured flow path, and a liquid standard sample may be introduced by the pulse valve in the case where a sample to be measured is a liquid, and a gas standard sample may be introduced by the pulse valve in the case where a sample to be measured is a gas.

In the mass spectrometer according to the present invention, a sample to be measured and a standard sample can be arranged alternately in the flow path. At this time, a number of LC units or GC units may be linked.

In addition, in the above-described invention, an additional pulse valve that introduces a mobile phase intermittently may be arranged in the above-described standard sample flow path, and a liquid mobile phase may be introduced by the additional pulse valve in the case where a sample to be measured is a liquid, and a gas mobile phase may be introduced by the additional pulse valve in the case where a sample to be measured is a gas.

Figure 7:
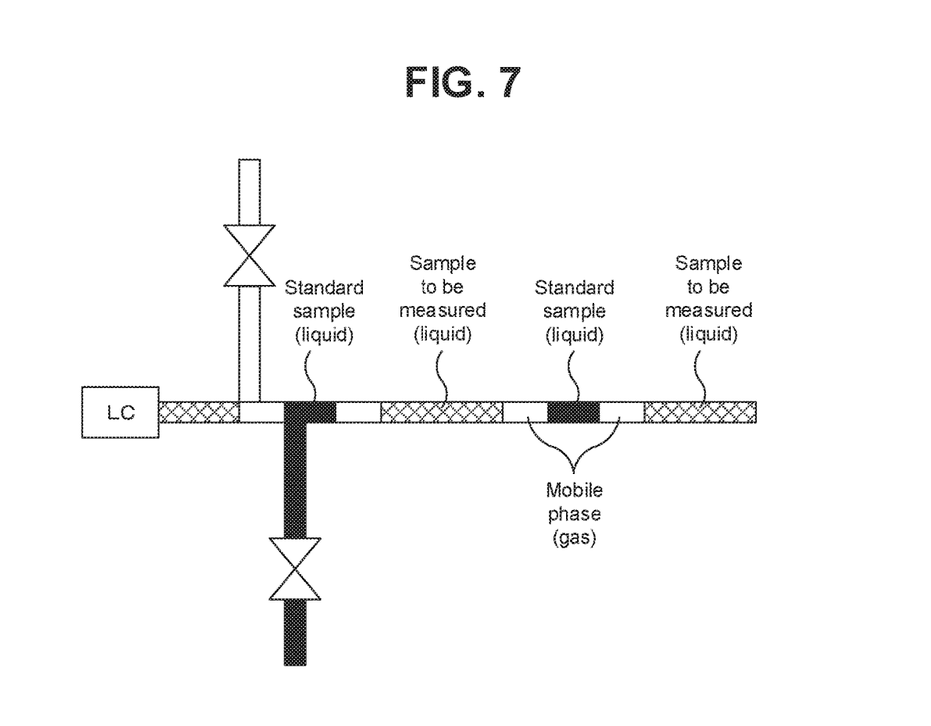
FIG. 7 is a diagram illustrating an example of a flow path when mobile phases are injected.

In the mass spectrometer according to the present invention, a mobile phase can be injected between a sample to be measured and a standard sample in a flow path so that the sample to be measured and the standard sample do not mix in the flow path. FIG. 7 shows an example of a flow path when such mobile phases are injected.

DESCRIPTION OF EMBODIMENTS

In the following, the embodiments of the present invention are described in reference to the drawings. The present invention is not limited to the below-described embodiments, and various modifications can, of course, be included as long as the gist of the invention is not deviated from.

<First Embodiment>

Figure 1:
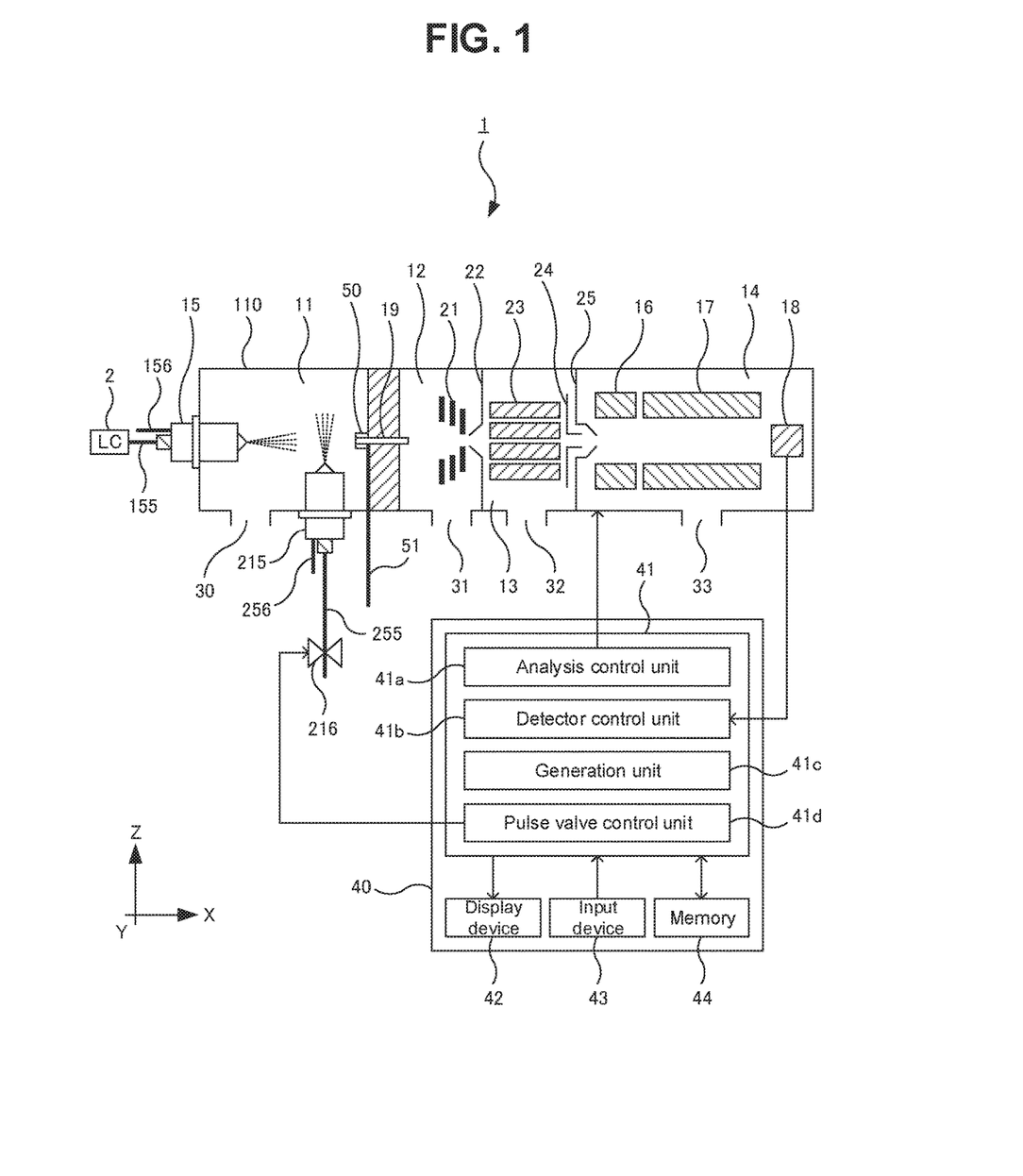
FIG. 1 is a schematic diagram showing the structure of the liquid chromatograph mass spectrometer using an ESI method according to the first embodiment of the present invention.

FIG. 1 is a schematic diagram showing the structure of the liquid chromatograph mass spectrometer using an ESI method according to the first embodiment. Here, the same symbols are attached to the same components as in the above-described conventional liquid chromatograph mass spectrometer 201.

A liquid crystal chromatograph mass spectrometer 1 is provided with an LC unit 2, a probe (ion source for sample to be measured) 15, a probe (ion source for standard sample) 215, a pulse valve 216, an ionization chamber 11 having a chamber (housing) 110, a first middle chamber 12 that is adjacent to the ionization chamber 11, a second middle chamber 13 that is adjacent to the first middle chamber 12, a mass spectrometry chamber (MS unit) 14 that is adjacent to the second middle chamber 13, and a computer 40 that controls the entirety of the liquid chromatograph mass spectrometer 1.

The ionization chamber 11 is provided with a chamber 110 in a rectangular parallelepiped form of 13 cm×13 cm×12 cm, and the chamber 110 has an upper wall, a partition (rear wall), a front wall, a right side wall, a left side wall and a lower wall. Thus, the space inside the ionization chamber 11 is surrounded by the upper wall, the partition, the front wall, the right side wall, the left side wall and the lower wall.

A circular opening that runs in the forward and backward directions (X direction) is created in the front wall so that the probe 15 is attached in this opening.

A circular opening that runs in the upward and downward directions (Z direction) is created in the lower wall, and the probe 215 is attached in this opening.

The probe 215 has the same shape as the probe 15 in FIG. 5A and has a double tube structure so that the standard sample that is supplied through the standard sample flow path 255 is jetted from the inside of the circular tube. Meanwhile, the nitrogen gas that is supplied from the nebulizing gas flow path 256 is jetted between the circular tube and the nozzle in a circular tube form. As a result, the jetted standard sample is converted to an atomized state through the collision with the nebulizing gas that is jetted around the circular tube, and thus is sprayed.

In addition, a high voltage of several kV is applied to the tip of the nozzle from the wires connected to the voltage supply so that ionization can be carried out.

A standard sample where the peaks of fragment ions regularly appear is useful, and a standard sample having a low molecular amount such as PFTBA (perfluorotributylamine) is used in a region of a low mass-to-charge ratio (m/z), for example. Meanwhile, a standard sample having a high molecular amount such as triazine (tris-(perfluoroheptyl)-s-triazine) and PFK (perfluorokerosene) are used in a region of a high mass-to-charge ratio (m/z) where the mass-to-charge ratio (m/z) is approximately 700 or greater.

The partition is arranged so as to partition the inside of the ionization chamber 11 from the inside of the first middle chamber 12. A solvent releasing tube (ion introducing tube) 19 in a circular tube form (having an outer diameter of 1.6 mm and an inner diameter of 0.5 mm) is formed in the partition, and a dry gas flow path 50 is formed so as to cover the surrounding of the solvent releasing tube 19. As a result, the inside of the ionization chamber 11 and the inside of the first middle chamber 12 communicate via the solvent releasing tube 19. In addition, the solvent releasing tube 19 functions to accelerate solvent releasing and ionization through the application of heat and through the collision when ions and microscopic droplets of the sample that have been sprayed from the probe 15 or the probe 215 pass through the inside of the solvent releasing tube 19. Furthermore, the solvent releasing tube 19 is dried by a dry gas when wet with a sample to be measured or a standard sample.

The nozzle of the probe 15 is directed toward the front (X direction) so as to face the entrance of the solvent releasing tube 19 at a predetermined distance (2 cm, for example) in between. In addition, the nozzle of the probe 215 is directed upward (Z direction) so as to spray a standard sample between the nozzle of the probe 15 and the entrance of the solvent releasing tube 19 at a predetermined flow rate (0.1 ml/min, for example). As a result, the standard sample blows away the sample to be measured that is directed toward the solvent releasing tube 19 when the standard sample is sprayed so that only the standard sample is introduced into the solvent releasing tube 19.

A drain 30 is created in the lower wall so that unnecessary samples can be discharged to the outside through the drain 30.

An example of the pulse valve 216 arranged in the standard sample flow path 255 is one that is made by Musashi Engineering Co., LTD. Thus, the pulse valve 216 is switched by a control signal from the computer 40 so as to be either in an open state where a standard sample is introduced into the standard sample flow path 255 or in a closed state where a standard sample is not introduced.

The computer 40 is provided with a CPU 41, a display device 42, an input device 43 and a memory 44. In addition, the processes in the CPU 41 can be described as function blocks that include an analysis control unit 41$a$ that controls quadrupoles 16 and 17 through the input operation by a user, a detector control unit 41$b$ that acquires an intensity signal from the detector 18, a generation unit 41$c$ that generates a mass spectrum, which is then stored in the memory 44, and a pulse valve control unit 41$d$ that controls the pulse vale 216 through the input operation by a user.

The pulse valve control unit 41$d$ controls the pulse valve 216 on the basis of the input signal from the input device 43. In the case where the period of time between the measurement start time $t_1$ and the measurement end time $t_2$ is 31 minutes, and an input signal for the open state is inputted for one minute for every nine minutes, for example, a pulse signal (control signal) for introducing a standard sample of a predetermined amount is outputted to the pulse valve 216 from $t_1$ to $t_1+1$ minute, from $t_1+10$ minutes to $t_1+11$ minutes, from $t_1+20$ minutes to $t_1+21$ minutes, and from $t_1+30$ minutes to $t_1+31$ minutes, which is four times in total (see FIG. 6). Here, it is possible to change the contents of the conditions for the pulse signal through the input operation by a user, and thus, the operation time (introduction time) and the period of time of introduction (amount of introduction) can be set freely.

The generation unit 41$c$ controls the generation of a mass spectrum on the basis of the intensity signal acquired by the detector control unit 41$b$ and allows the memory 44 to store the mass spectrum. This operation is in sync with the operation of the pulse valve 216 on the basis of the input signal inputted into the pulse valve control unit 41$d$ so that the mass spectrum of a sample to be measured and the mass spectrum of a standard sample are separately stored in the memory 44. Thus, the values measured for each peak that are gained by measuring the sample to be measured (mass-to-charge ratio (m/z) and intensity value) are determined using the peaks that are gained by measuring the standard sample, and the mass spectrum of the standard sample of which the time is closest to the time when the mass spectrum of a sample to be measured is gained is selected as the mass spectrum of the standard sample. For example, the mass spectrum of the standard sample that is gained from $t_1$ to $t_1+1$ minute is used as the mass spectrum of a sample to be measured that is gained from $t_1+1$ minute to $t_1+5$ minutes, the mass spectrum of the standard sample that is gained from $t_1+10$ minutes to $t_1+11$ minutes is used as the mass spectrum of a sample to be measured that is gained from $t_1+5$ minutes to $t_1+10$ minutes and from $t_1+11$ minutes to $t_1+15$ minutes, the mass spectrum of the standard sample that is gained from $t_1+20$ minutes to $t_1+21$ minutes is used as the mass spectrum of a sample to be measured that is gained from $t_1+15$ minutes to $t_1+20$ minutes and from $t_1+21$ minutes to $t_1+25$ minutes, and the mass spectrum of the standard sample that is gained from $t_1+30$ minutes to $t_1+31$ minutes is used as the mass spectrum of a sample to be measured that is gained from $t_1+25$ minutes to $t_1+30$ minutes. As a result, it is possible to acquire a precise mass spectrum for each sample to be measured even in the case where a number of types of samples to be measured are introduced into the ionization chamber 11 one after another over a short period of time.

As described above, in the liquid chromatograph mass spectrometer 1 according to the first embodiment, the time at which a standard sample is introduced can be controlled appropriately while preventing a sample to be measured and the standard sample from mixing.

It is also possible to adjust the concentration of the standard sample that is introduced into the solvent releasing tube 19 by changing the amount of the standard sample that is introduced into the standard sample flow path 255 through the control of the pulse valve 216 at the time of the introduction of the standard sample.

<Second Embodiment>

Figure 2:
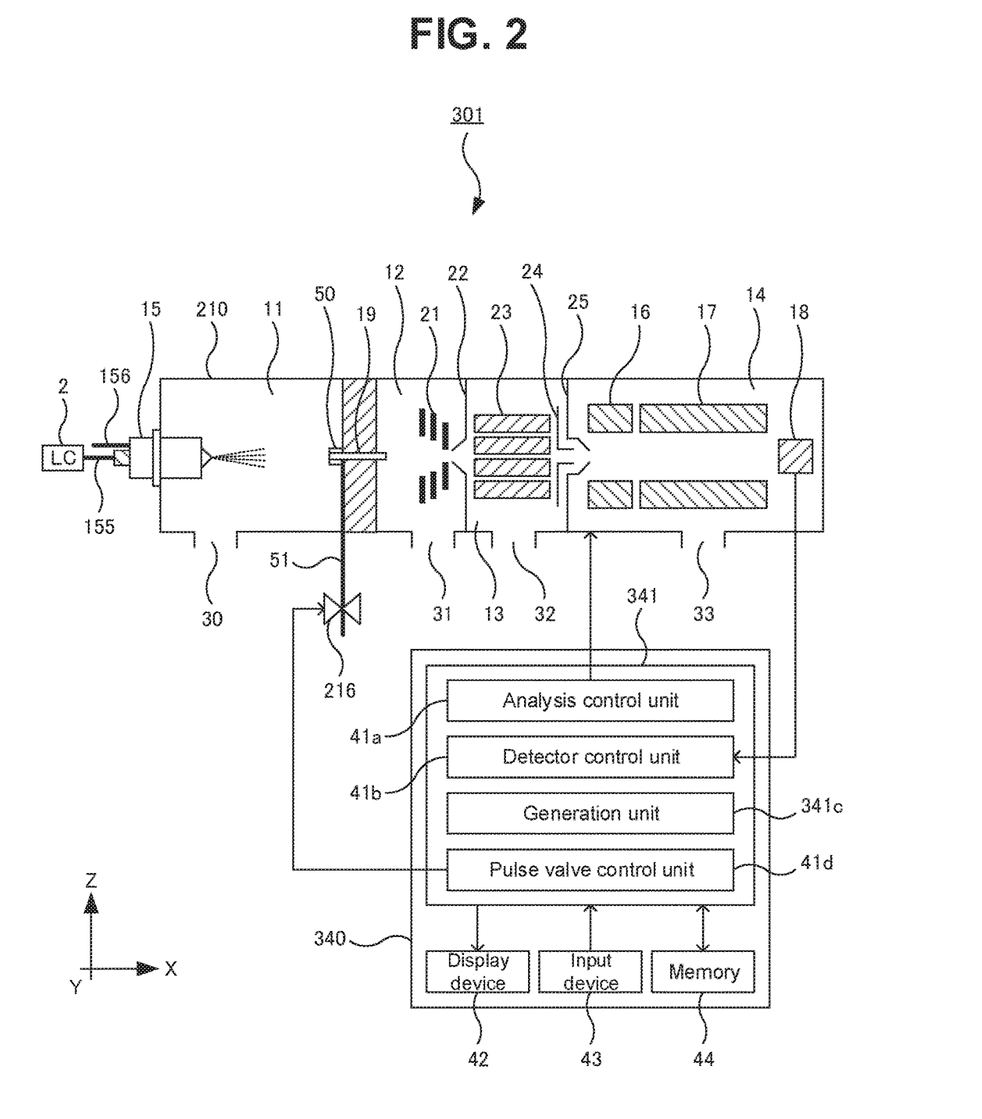
FIG. 2 is a schematic diagram showing the structure according to the second embodiment of the present invention.

FIG. 2 is a schematic diagram showing the configuration of the liquid chromatograph mass spectrometer using an ESI method according to the second embodiment. Here, the same symbols are attached to the same components as in the liquid chromatograph mass spectrometers 1 and 201.

The liquid chromatograph mass spectrometer 301 is provided with an LC unit 2, a probe (ion source for sample to be measured) 15, a pulse valve 216, an ionization chamber 11 having a chamber (housing) 210, a first middle chamber 12 that is adjacent to the ionization chamber 11, a second middle chamber 13 that is adjacent to the first middle chamber 12, a mass spectrometry chamber (MS unit) 14 that is adjacent to the second middle chamber 13, and a computer 340 that controls the entirety of the liquid chromatograph mass spectrometer 301.

The pulse valve 216 is arranged in a dry gas flow path (standard sample flow path) 51. As a result, the standard sample blows away the sample to be measured directed toward the solvent releasing tube 19 when the standard sample is sprayed, and thus, only the standard sample is introduced into the solvent releasing tube 19. In addition, the pulse valve 216 is switched when a control signal is inputted from the computer 340 so as to be either in an open state where a standard sample is introduced into the dry gas flow path 51 or in a closed state where a standard sample is not introduced.

The computer 340 is provided with a CPU 341, a display device 42, an input device 43 and a memory 44. Furthermore, the processes in the CPU 341 can be described as function blocks that include an analysis control unit 41a that controls quadrupoles 16 and 17 through the input operation by a user, a detector control unit 41b that acquires an intensity signal from the detector 18, a generation unit 341c that generates a mass spectrum, which is then stored in the memory 44, and a pulse valve control unit 41d that controls the pulse vale 216 through the input operation by a user.

The generation unit 341c controls the generation of a mass spectrum on the basis of the intensity signal acquired by the detector control unit 41b and allows the memory 44 to store the mass spectrum. Thus, the mass-to-charge ratio (m/z) for each peak that is gained by measuring a sample to be measured is determined by using the peak that is gained by measuring a standard sample. The two mass spectra, one is before and the other is after the time when the mass spectrum for a sample to be measured is gained, that sandwich the time at which the mass spectrum of the sample to be measured is gained are used as the mass spectra of the standard sample.

As described above, in the liquid chromatograph mass spectrometer 301 according to the second embodiment, the time at which a standard sample is introduced can be controlled appropriately by preventing a sample to be measured and the standard sample from mixing. It is also possible to adjust the concentration of the standard sample that is introduced into the solvent releasing tube 19 by changing the amount of the standard sample that is introduced into the dry gas flow path 51 through the control of the pulse valve 216 at the time of the introduction of the standard sample.

<Third Embodiment>

Figure 3:
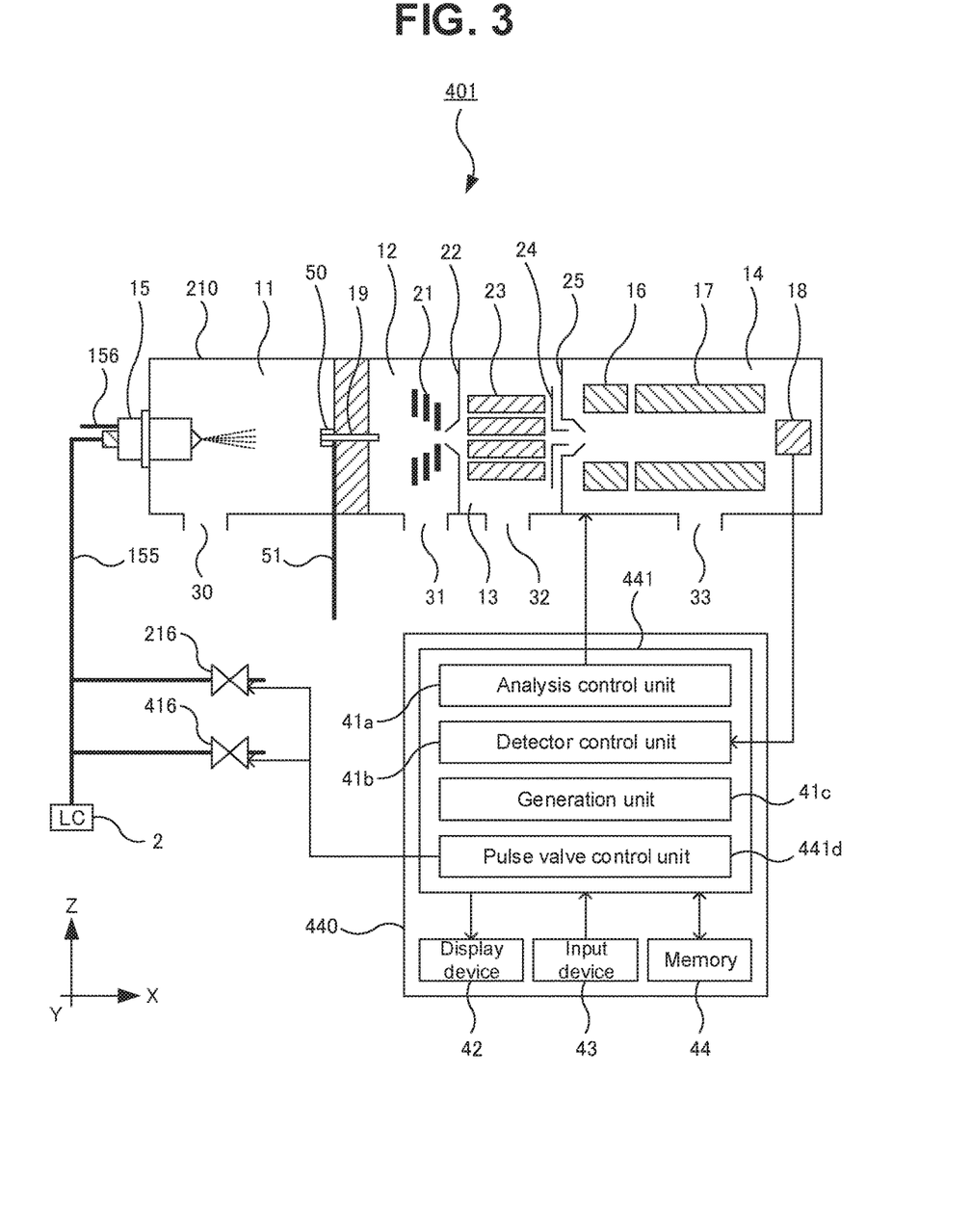
FIG. 3 is a schematic diagram showing the structure according to the third embodiment of the present invention.

FIG. 3 is a schematic diagram showing the configuration of the liquid chromatograph mass spectrometer using an ESI method according to the third embodiment. Here, the same symbols are attached to the same components as in the liquid chromatograph mass spectrometer 1.

The liquid chromatograph mass spectrometer 401 is provided with an LC unit 2, a probe (ion source for sample to be measured) 15, a pulse valve 216, a pulse valve 416, an ionization chamber 11 having a chamber (housing) 210, a first middle chamber 12 that is adjacent to the ionization chamber 11, a second middle chamber 13 that is adjacent to the first middle chamber 12, a mass spectrometry chamber (MS unit) 14 that is adjacent to the second middle chamber 13, and a computer 440 that controls the entirety of the liquid chromatograph mass spectrometer 401.

The pulse valve 216 is arranged in the sample to be measured flow path (standard sample flow path) 155. Thus, the pulse valve 216 is switched when a control signal is inputted from the computer 440 so as to be either in an open state where a predetermined amount of standard sample is introduced into the sample to be measured flow path 155 or in a closed state where a standard sample is not introduced.

In addition, the pulse valve 416 is arranged in the sample to be measured flow path 155 in a stage before the pulse valve 216 in the sample to be measured flow path 155. Thus, the pulse valve 416 is switched when a control signal is inputted from the computer 440 so as to be either in an open state where a predetermined amount of gas (mobile phase) is introduced into the sample to be measured flow path 155 or in a closed state where a gas (mobile phase) is not introduced.

As a result, a gas (mobile phase) can be injected between a sample to be measured and a standard sample in the sample to be measured flow path 155 so that the sample to be measured and the standard sample do not mix in the sample to be measured flow path 155 (see FIG. 7).

The computer 440 is provided with a CPU 441, a display device 42, an input device 43 and a memory 44. In addition, the processes in the CPU 441 can be described as function blocks that include an analysis control unit 41a that controls quadrupoles 16 and 17 through the input operation by a user, a detector control unit 41b that acquires an intensity signal from the detector 18, a generation unit 41c that generates a mass spectrum, which is then stored in the memory 44, and a pulse valve control unit 441d that controls the pulse vale 216 and the pulse valve 416 through the input operation by a user.

As described above, in the liquid chromatograph mass spectrometer 401 according to the third embodiment, the time at which a standard sample is introduced can be controlled appropriately by preventing a sample to be measured and the standard sample from mixing. In addition, a gas (mobile phase) can be injected so that one sample to be measured and another sample to be measured do not mix in the sample to be measured flow path 155, and therefore, a number of LC units may be linked to the sample to be measured flow path 155.

<Other Embodiments>

(1) Though the liquid chromatograph mass spectrometer 301 has a configuration where the pulse valve 216 is arranged in the dry gas flow path 51 as described above, such a configuration is possible where the pulse valve 216 is arranged in the nebulizing gas flow path 156.

(2) Though the configurations of liquid chromatograph mass spectrometers are described above, the configurations may be applied to gas chromatograph mass spectrometers.

INDUSTRIAL APPLICABILITY

The present invention is applicable to a calibration method for a mass spectrometry unit in a chromatograph mass spectrometer, for example.

REFERENCE SIGNS LIST 1 liquid chromatograph mass spectrometer
11 ionization chamber
14 mass spectrometry chamber (mass spectrometry unit)
15 probe
19 solvent releasing tube (ion introducing tube)
110 chamber (housing)
155 sample to be measured flow path
216 pulse valve
255 standard sample flow path

The invention claimed is:

1. A mass spectrometer, comprising:
an ionization chamber where a sample is ionized, and
a mass spectrometry unit into which ions are introduced from the ionization chamber, wherein
said ionization chamber has a housing that provides a space inside the housing,
a probe having a sample to be measured flow path in order to spray a sample to be measured into the inside of said ionization chamber is attached to said housing, and an ion introducing tube is created in said housing so that the inside of said ionization chamber and the inside of the mass spectrometry unit communicate,
a mass spectrum value that is gained by measuring a sample to be measured is calibrated using a mass spectrum value that is gained by measuring the standard sample, and
the mass spectrometer further comprises a standard sample flow path that sprays the standard sample into the inside of said ionization chamber, and a pulse valve that is arranged in a standard sample flow path so as to introduce the standard sample intermittently, and
said standard sample flow path has a nozzle arranged in such a manner that said standard sample is sprayed between the spraying nozzle of said sample to be measured flow path and said ion introducing tube with respect to a blowing direction of the sample to be measured that has been sprayed from the spraying nozzle.

2. The mass spectrometer according to claim 1, characterized in that said standard sample flow path is the same flow path as a dry gas flow path that sprays a dry gas.

3. A mass spectrometer, comprising:
an ionization chamber where a sample is ionized, and
a mass spectrometry unit into which ions are introduced from the ionization chamber, wherein
said ionization chamber has a housing that provides a space inside the housing,
a probe having a sample to be measured flow path in order to spray a sample to be measured into the inside of said ionization chamber is attached to said housing, and an ion introducing tube is created in said housing so that the inside of said ionization chamber and the inside of the mass spectrometry unit communicate,
a mass spectrum value that is gained by measuring a sample to be measured is calibrated using a mass spectrum value that is gained by measuring a standard sample, and
the mass spectrometer further comprising
a standard sample flow path that is branched from a first branching point in a middle of said sample to be measured flow path and into which a standard sample is intermittently introduced via a first pulse valve; and
a flow path that is branched from a second branching point in a rear stage father from a spraying location of the probe than the first branching point in the middle of said sample to be measured flow path and into which a gas mobile phase is injected intermittently via a second pulse valve,
wherein a sample to be measured and a standard sample are introduced alternately with a gas mobile phase in between the sample to be measured and the standard sample so that the sample to be measured and the standard sample are not be mixed with each other.

* * * * *